(12) United States Patent
Simoneau

(10) Patent No.: US 6,322,820 B1
(45) Date of Patent: Nov. 27, 2001

(54) COMPOSITION OF MATTER AND METHOD FOR THE RELIEF OF HEMORRHOIDAL CONDITIONS

(76) Inventor: Sylvain Simoneau, 1495 Evergreen, St-Bruno, Quebec (CA), J3V 4C6

( * ) Notice: Subject to any disclaimer, the term of this patent is extended or adjusted under 35 U.S.C. 154(b) by 0 days.

(21) Appl. No.: 09/575,626

(22) Filed: May 22, 2000

(30) Foreign Application Priority Data

May 25, 1999 (CA) .................................................. 2272732

(51) Int. Cl.⁷ .......................... A61K 33/30; A61K 31/05; A61K 31/045; A61K 31/56; A61K 9/06
(52) U.S. Cl. .................. 424/642; 424/641; 424/DIG. 15; 514/171; 514/179; 514/729; 514/734; 514/783; 514/786; 514/789; 514/882; 514/966; 514/969
(58) Field of Search .................................... 424/641, 642, 424/DIG. 15; 514/729, 734, 171, 179, 783, 786, 789, 882, 966, 969

(56) References Cited

U.S. PATENT DOCUMENTS 5,858,371 * 1/1999 Singh et al. ...................... 424/195.1

OTHER PUBLICATIONS

Martindale The Extra Pharmacopoeia, The Pharmaceutical Press, London, pp. 771–772, 1334, 1627, 1993.*

* cited by examiner

*Primary Examiner*—John Pak
(74) *Attorney, Agent, or Firm*—Eric Fincham

(57) ABSTRACT

A composition of matter for treating hemorrhoids comprising a pharmaceutically acceptable carrier, between 1% and 10% by weight of zinc oxide, between 0.2% and 5% by weight of resorcinol and between 0.1% and 3% by weight of menthol. A preferred carrier is white petroleum jelly and the composition may further include hydrocortisone as an active ingredient.

15 Claims, No Drawings

COMPOSITION OF MATTER AND METHOD FOR THE RELIEF OF HEMORRHOIDAL CONDITIONS

The present invention relates to novel methods and compositions for the relief of hemorrhoidal conditions.

BACKGROUND OF THE INVENTION

Hemorrhoids are the result of swollen, normally present blood vessels in and around the anus and lower rectum. When these normally present veins become abnormally enlarged or dilated, they are called hemorrhoids (also known as hemorrhoids or piles). In this respect, they have been compared to varicose veins in the legs. Hemorrhoids may be either inside the anus (internal) or under the skin around the anus (external).

Hemorrhoids are extremely common in both the male and female populations with it being reported that the majority of people will have experience of or problems from hemorrhoids during their life. Symptoms of hemorrhoids include anal bleeding while some external hemorrhoids may cause painful swelling or a hard lump. Hemorrhoids are usually not dangerous or life threatening although it is important that they be evaluated to exclude more serious causes of the symptoms such as polyps and cancer.

A great deal of the medical treatment of hemorrhoids is aimed at relieving the symptoms and these can include warm tub or sitz baths, ice packs to reduce swelling and application of a hemorrhoidal cream or suppository to the affected area for a limited time. This may be accompanied by changes to the diet and it is often recommended to increase the amount of fiber and fluids in the diet to result in softer bulkier stools to eliminate the pressure on the hemorrhoids.

Surgical treatment includes rubber band ligation to cut off circulation to the hemorrhoid whereby it withers away within a few days. Sclerotherapy comprises the injection of a chemical solution around the blood vessel to shrink the hemorrhoid. Other techniques used may include electrical or laser heat or in the case of more extensive or severe hemorrhoids, an operation called an hemorrhoidectomy may be performed.

As aforementioned, there are certain creams and suppositories which are known in the art to relieve the symptoms of hemorrhoids.

SUMMARY OF THE INVENTION

It is an object of the present invention to provide a hemorrhoidal cream which is simple to manufacture and is effective against the symptoms of hemorrhoids.

According to one aspect of the present invention, there is provided a composition of matter for treating hemorrhoids, the composition of matter comprising a pharmaceutically acceptable carrier, between about 1% and about 10% by weight of zinc oxide, between about 0.2% and about 5% by weight of resorcinol, and between about 0.1% and about 3% by weight of menthol.

In a further aspect of the present invention, there is provided a composition of matter for treating hemorrhoids, the composition of matter comprising a pharmaceutically acceptable carrier, between about 2% and about 8% by weight of zinc oxide, between about 0.4% and about 3% by weight of resorcinol, and between about 0.2% and about 2% by weight of menthol.

In a further aspect of the present invention, there is provided a method for the treatment of hemorrhoids, the method comprising the step of applying to an affected area a cream comprising a pharmaceutically acceptable carrier, between about 1% and about 10% by weight of zinc oxide, between about 0.2% and about 5% by weight of resorcinol, and between about 0.1% and about 3% by weight of menthol.

DESCRIPTION OF THE PREFERRED EMBODIMENTS

A composition of the present invention has, as set forth above, active ingredients comprised of zinc oxide, resorcinol, and menthol. Optionally, the composition may also include hydrocortisone.

The zinc oxide is present in an amount of between about 1% and about 10% by weight and preferably between about 2% and about 8% by weight. Even more preferably, the zinc oxide is present in an amount of between about 3% and about 7% by weight.

The resorcinol is present in an amount of between about 0.2% and about 5% by weight and preferably between about 0.4% and about 3% by weight. Even more preferably, the resorcinol is present in an amount of between about 0.5% and about 2% by weight.

The menthol is present in an amount of between about 0.1% and about 3% by weight and preferably between about 0.2% and about 2% by weight. Even more preferably, the menthol is present in an amount of between about 0.3% and about 1% by weight.

The composition may include further active ingredients. Thus, the composition may also include hydrocortisone, the hydrocortisone being present in an amount of between 0.1% and 3% by weight and more preferably, being present in an amount of between 0.5% and 2% by weight.

The carrier may be any suitable and the composition may be in the form of either a cream or ointment. Carriers can include glycerin or waxes with a preferred carrier being white petroleum jelly, the petroleum jelly being present in an amount of between 76% and 98.7% by weight. Alternatively, the composition may be incorporated in a suppository.

The composition may be applied either by an applicator or other means although if the applicator increases pain, it should not be used. The affected area should be washed prior to applying the product. The product should be applied morning and evening with not more than six applications per day. Alternatively, the composition could be incorporated in a substrate as a "wipe" and then applied.

The preparation of the composition may be carried out according to conventional methods. Thus, the active substances and auxiliary or carrier substances may be suitably mixed by stirring or homogenization using conventional devices. The incorporation of the active ingredients can be carried out at elevated temperatures in order to facilitate the process. To this end, one may use other inert carrier materials to assist in the process. One such material would be sweet almond oil into which the resorcinol is dissolved. The almond oil may be present in an amount of between 1% and 4% by weight.

Preferably, the resorcinol is incorporated in the almond oil at a temperature of between 60° C. and 90° C. The composition of resorcinol and sweet almond oil is then added to white petroleum jelly which is at a temperature of between 30° C. and 60° C.

Subsequently, the zinc oxide and the menthol may be added and the product cooled.

EXAMPLE 1

A cream is made by mixing the following ingredients:

|  | By Weight |
| --- | --- |
| Zinc oxide | 5.0% |
| Resorcinol | 1.0% |
| Menthol | 0.6% |
| Almond Oil | 2.6% |

In a suitable stainless steel container, the almond oil is heated to a temperature of approximately 85° C. and then the resorcinol is dissolved therein. The temperature is then maintained at approximately 80° C.

The petroleum jelly is heated to approximately 50° C. and then the solution of resorcinol and almond oil is placed therein. The composition is then maintained at 50° C. and the zinc oxide and then the menthol are added while stirring. The stirring is continued while the composition is cooled to approximately 28° C.

EXAMPLE 2

A male patient suffering from hemorrhoids with an associated abscess at the anal opening was treated during a period of four months with the ointment of Example 1. After four months, there was no further evidence of hemorrhoids.

EXAMPLE 3

A patient diagnosed as having hemorrhoids and anal rectal spasms was treated for a period of one month with the ointment of Example 1. A further examination revealed no further symptoms.

EXAMPLE 4

A female patient diagnosed with hemorrhoids was treated with the ointment of Example 1 for a period of three weeks. After this period of time, an examination revealed no signs of hemorrhoids.

It will be understood that the above described embodiments are for purposes of illustration only and that changes and modifications may be made thereto without departing from the spirit and scope of the invention.

I claim:

1. A composition of matter for treating hemorrhoids, said composition of matter comprising a pharmaceutically acceptable carrier and pharmaceutically active ingredients, said pharmaceutically active ingredients consisting essentially of, between about 1% and about 10% by weight of zinc oxide, between about 0.2% and about 5% by weight of resorcinol, and between about 0.1% and about 3% by weight of menthol.

2. The composition of claim 1 wherein said zinc oxide is present in an amount of between about 2% and about 8% by weight.

3. The composition of claim 2 wherein said zinc oxide is present in an amount of between about 3% and about 7% by weight.

4. The composition of claim 1 wherein said resorcinol is present in an amount of between about 0.4% and about 3% by weight.

5. The composition of claim 4 wherein said resorcinol is present in an amount of between about 0.5% and about 2% by weight.

6. The composition of claim 1 wherein said menthol is present in an amount of between about 0.2% and about 2% by weight.

7. The composition of claim 6 wherein said menthol is present in an amount of between about 0.3% and about 1% by weight.

8. The composition of claim 1 wherein said carrier is petroleum jelly.

9. The composition of claim 8 further including between about 1% and about 4% by weight of almond oil.

10. The composition of claim 1 wherein said composition comprises between about 2% and about 8% by weight of zinc oxide, between about 0.4% and about 3% by weight of resorcinol, and between about 0.2% and about 2% by weight of menthol.

11. The composition of claim 10 wherein said pharmaceutically acceptable carrier is white petroleum jelly.

12. The composition of claim 11 further including almond oil present in an amount of between about 1% and about 4% by weight.

13. A method for the treatment of hemorrhoids comprising the step of applying to the area affected a therapeutically effective amount of the composition of claim 1.

14. A composition of matter for treating hemorrhoids, said composition of matter comprising a pharmaceutically acceptable carrier and pharmaceutically active ingredients, said pharmaceutically active ingredients consisting essentially of, between about 1% and about 10% by weight zinc oxide, between about 0.2% and about 5% by weight of resorcinol, between about 0.1% and about 3% by weight menthol, and between about 0.1% and about 2% by weight of hydrocortisone.

15. A method for the preparation of a composition of matter for treating hemorrhoids, said composition of matter comprising a pharmaceutically acceptable carrier, between about 1% and about 10% by weight of zinc oxide, between about 0.2% and about 5% by weight of resorcinol, and between about 0.1% and about 3% by weight of menthol; said method comprising the steps of dissolving said resorcinol in sweet almond oil at a temperature of between 60° C. and 90° C.; subsequently adding said resorcinol and said sweet almond oil to white petroleum jelly at a temperature of between 30° C. and 60° C.; and subsequently mixing said zinc oxide and said menthol therewith.

\* \* \* \* \*